United States Patent [19]

Harandi et al.

[11] Patent Number: 5,260,493
[45] Date of Patent: Nov. 9, 1993

[54] EFFLUENT TREATMENT FOR ETHER PRODUCTION

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 907,909

[22] Filed: Jul. 2, 1992

[51] Int. Cl.$^5$ .............................................. C07C 41/06
[52] U.S. Cl. ................................................... 568/697
[58] Field of Search ........................................ 568/667

[56] References Cited

U.S. PATENT DOCUMENTS

| | | | |
|---|---|---|---|
| 4,544,776 | 10/1985 | Osterburg et al. | 568/697 |
| 4,665,237 | 5/1987 | Arakawa et al. | 568/697 |
| 4,827,046 | 5/1989 | Harandi et al. | 585/310 |
| 4,831,195 | 5/1989 | Harandi et al. | 568/697 |

FOREIGN PATENT DOCUMENTS 2185754A 1/1987 United Kingdom .

*Primary Examiner*—Howard T. Mars
*Attorney, Agent, or Firm*—Alexander J. McKillop; L. G. Wise

[57] ABSTRACT

A continuous process for converting lower aliphatic alkanol and light olefinic hydrocarbon feedstock rich in tertiary olefins, such as isobutylene and other C$_4$ isomeric hydrocarbons, to alkyl tertiary-alkyl ethers and C$_5$+ gasoline boiling range hydrocarbons. An improved process and reactor system includes means for: washing the olefinic hydrocarbon feedstock with an aqueous liquid stream in a contactor unit to recover water-soluble impurities therefrom in a washwater stream recovered from the contactor unit; contacting the lower aliphatic alkanol and a washed light olefinic hydrocarbon stream from the contactor unit under iso-olefin etherification conditions in at least one etherification reaction zone containing acid etherification catalyst; separating etherification effluent to recover a light primary effluent stream comprising unreacted alkanol and light olefinic hydrocarbon and a liquid product stream containing alkyl tertiary-butyl ether; contacting at least one effluent stream containing unreacted alkanol and light olefinic hydrocarbon with a substantially fresh water liquid extractant stream to recover unreacted alkanol therein. In a preferred embodiment, at least a portion of the alkanol-containing liquid extract stream is passed to the washing step for treatment of hydrocarbon feedstock.

25 Claims, 2 Drawing Sheets

EFFLUENT TREATMENT FOR ETHER PRODUCTION

BACKGROUND OF THE INVENTION

This invention relates to methods for reacting aliphatic alcohol (alkanol), such as methanol or the like and olefinic hydrocarbons to produce lower alkyl tertiary-alkyl ethers.

In particular, this invention relates to a continuous integrated system for converting methanol to high octane ether by etherifying hydrocarbons containing iso-olefins, such as the $C_3$-$C_5$ olefinic cracked gas streams obtained from fluid catalytic cracking (FCC) products.

It is known that isobutylene and other isoalkenes produced by hydrocarbon cracking may be reacted with methanol and other $C_1$-$C_4$ lower aliphatic alcohols over an acidic catalyst to provide methyl tertiary butyl ether (MTBE) or the like. Generally, it is known that asymmetrical ethers having the formula $(CH_3)_3C$-$O$-$R$, where R is a $C_1$-$C_4$ alkyl radical, are particularly useful as octane improvers for liquid fuels, especially gasoline.

MTBE, ethyl t-butyl ether (ETBE), tert-amyl methyl ether (TAME) and isopropyl t-butyl ether (IPTBE) are known to be high octane ethers. The article by J. D. Chase, et al., *Oil and Gas Journal*, Apr. 9, 1979, discusses the advantages one can achieve by using such materials to enhance gasoline octane. The octane blending number of MTBE when 10% is added to a base fuel ($R+O=91$) is about 120. For a fuel with a low motor rating ($M+O=83$) octane, the blending value of MTBE at the 10% level is about 103. On the other hand, for an $(R+O)$ of 95 octane fuel, the blending value of 10% MTBE is about 114.

While it is known that isobutylene and/or isoamylene may be reacted with methanol over an acidic catalyst to provide MTBE and/or TAME, a problem of major importance in these processes is the separation of unreacted methanol and hydrocarbons from the etherification reaction product due to the proclivity of methanol to form a very dilute azeotropic mixture with hydrocarbons and the strong solubility of methanol in both water and hydrocarbons. But, to achieve high iso-olefin conversion to ethers equimolar or larger quantities of methanol are preferred in the etherification reaction.

In recent years, a major development within the petroleum industry has been the discovery of the special catalytic capabilities of a family of zeolite catalysts based upon medium pore size shape selective metallosilicates. Discoveries have been made leading to a series of analogous processes drawn from the catalytic capability of zeolites. Depending upon various conditions of space velocity, temperature and pressure lower oxygenates, such as methanol can be converted in the presence of zeolite type catalysts to olefins which can oligomerize to provide gasoline or distillate or can be converted further to produce aromatics. Recognizing the commonality of the feedstock and product between etherification reactions to produce high octane gasoline and zeolite catalyzed conversion reactions, interest has focused on the applicability of combined processes as an approach to advance the art in the production of high octane gasoline. While methanol or other reactive alkanols are converted by zeolite catalysis, minor amounts of other oxygenates are produced in the conversion process. Ketones, aldehydes and alkanoic acids found in the hydrocarbon effluent may be deleterious to its use as fuel.

It has been discovered that under certain conditions substantial improvements in the art of alkyl tert-alkyl ether production can be realized in a combination or integration of etherification and hydrocarbon conversion processes based upon zeolite type catalysis. Accordingly, it is an object of this invention to provide a novel integrated process for the production of alkyl tert-alkyl ethers, particularly MTBE and/or TAME.

SUMMARY OF THE INVENTION

An improved process has been found for reacting alcohol feedstock with light olefinic hydrocarbons rich in tertiary olefins (i.e. isobutylene) to produce $C_5+$ alkyl tertiary-alkyl ether, which comprises:

contacting the alcohol (i.e. methanol) feedstock with olefinic hydrocarbon feedstock comprising predominantly isobutylene-rich mono-olefins in a primary stage reaction zone under etherification reaction conditions in the presence of acid etherification catalyst to produce a primary effluent comprising ether product, unreacted methanol and olefins;

separating ether product from unreacted methanol and olefins to provide a light etherification effluent stream.

Advantageously, at least a major portion of the unreacted methanol and light olefins is converted to $C_5+$ gasoline boiling range hydrocarbons in a secondary stage reaction zone in contact with acidic medium pore metallosilicate catalyst, with separation of secondary stage conversion effluent to recover a secondary light vapor stream comprising water-soluble oxygenates and light hydrocarbons and a liquid $C_5+$ hydrocarbon product stream.

Improved operation is achieved by contacting an oxygenate-containing effluent stream, such as the secondary light vapor stream, with an aqueous washing medium, such as substantially fresh water liquid extractant stream, to remove water-soluble oxygenates.

Preferably, the light olefinic hydrocarbon stream consists essentially of $C_4$ olefins and paraffins, and at least a portion of oxygenate-containing liquid extract stream is passed to the primary stage for washing pretreatment of hydrocarbon feedstock.

These and other advantages and features of the invention will be seen in the following description and in the drawings.

DETAILED DESCRIPTION OF THE INVENTION

Typical feedstock materials for etherification reactions include olefinic streams, such as $C_3$-$C_5$ FCC light cracked gas containing butene isomers, often in mixture with substantial amounts of propene, propane, n-butane and isobutane. The $C_4$ components usually contain a major amount of unsaturated compounds, such as 10-35% isobutylene, 25-55% linear butenes, and small amounts of butadiene. Also, $C_4+$ heavier olefinic hydrocarbon streams may be used, particularly mixtures of isobutylene and isoamylene. These aliphatic streams are produced in a variety of petroleum refinery operations such as catalytic cracking of gas oil or the like. Such olefinic streams often contain detrimental amounts of impurities such as nitrogen compounds. It is advantageous to pretreat the hydrocarbon etherification feedstock to remove such impurities prior to contacting etherification catalyst. This can be achieved in the present invention by using a guard bed upstream of the reaction section, as herein described.

Suitable alkanols include $C_1$-$C_4$ primary or secondary alcohols, including methanol, ethanol, 1-propanol, isopropanol, 1-butanol, 2-butanol and mixtures thereof. The dry methanol feedstream should preferably have a purity of about 99.8 wt %.

Figure 1:
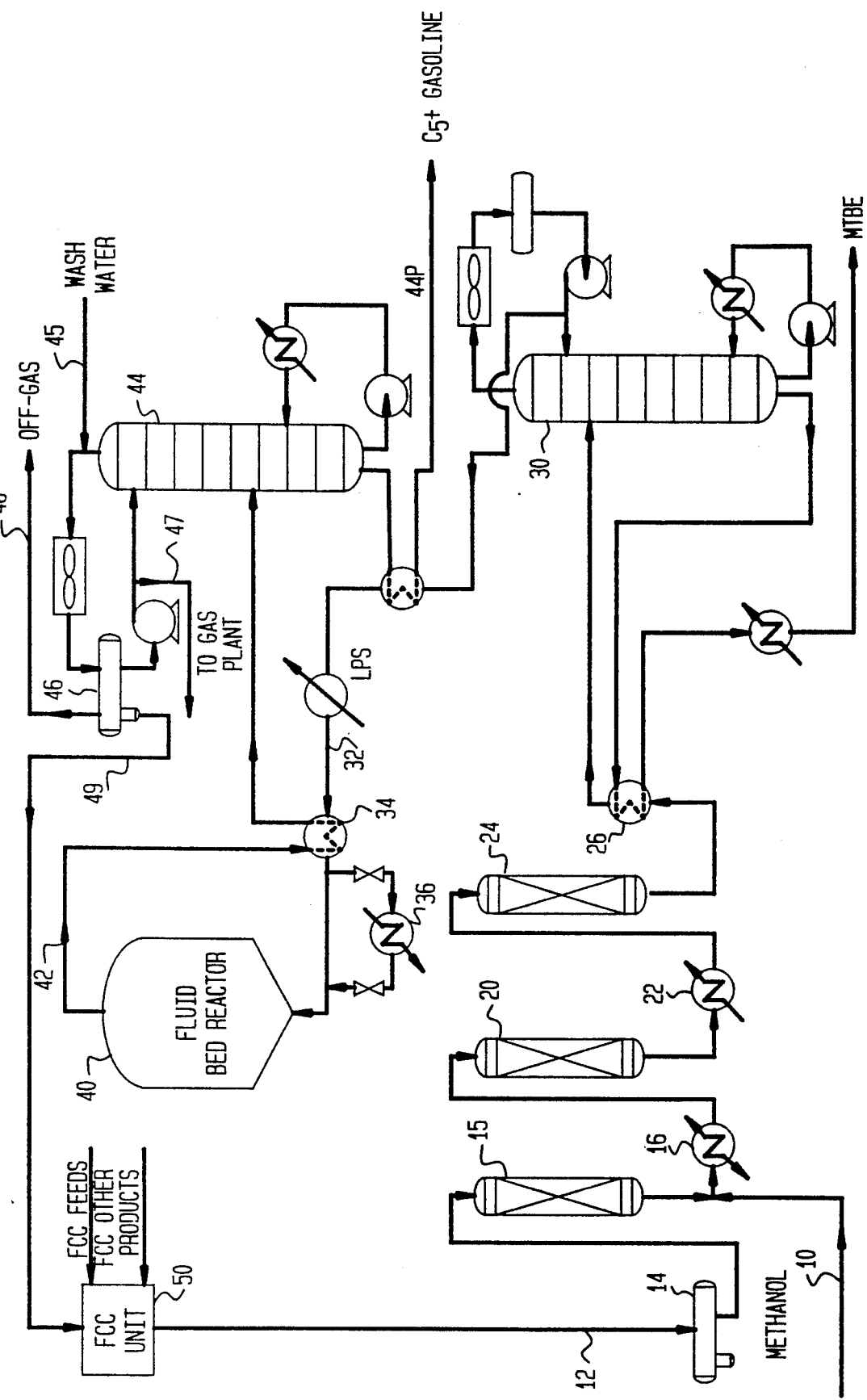
FIG. 1 of the drawing is a schematic etherification process flowsheet depicting a preferred embodiment of the present invention.

Referring to FIG. 1 of the drawing, a continuous stream of $C_3$-$C_5$ olefinic hydrocarbon liquid is introduced via conduit 12 to pre-separation unit 14 and guard bed 15 and mixed with dry methanol (MeOH) feedstock introduced via conduit 10. The combined stream which is at about 1190 kPa (170 psig), is heated in exchanger 16 to a temperature of about 55° C. (130° F.) and passed to a first serial reactor 20 for conversion of methanol in contact with acid etherification catalyst, preferably solid polysulfonic acid resin such as sulfonated vinyl aromatic resins. Amberlyst 15 from Rohm and Haas is a preferred catalyst. From first reactor 20 the reaction stream is cooled in exchanger 22 to about 55° C. and further reacted in a second serial reactor 24, where the reaction is carried partially to completion (e.g., 96% conversion of isobutylene).

The reactor effluent stream containing MTBE, methanol and unreacted light hydrocarbons is preheated in exchanger 26 and fed to debutanizer fractionation tower 30. In separation unit 30 the $C_5$+ methyl tert-alkyl ether product is recovered as a liquid product, along with byproduct dimer or other heavier hydrocarbons in the effluent. Tower overhead vapor comprising unreacted $C_4$- light hydrocarbons and methanol are passed via conduit 32 and heat exchange means 34, 36 to an effluent upgrading reactor 40. The catalytic conversion unit 40 is preferably a fluid bed unit. Reactor effluent stream 42 is fractionated in a debutanizer tower 44 to recover a gasoline product stream 44P. The overhead vapor from tower 44 is mixed with a liquid wash water stream 45. Water is used to extract a major portion of the unconverted methanol and other oxygenates including formic acid and other acidic compounds formed during the course of methanol reaction in reactor 40 to meet product purity requirements and prevent equipment corrosion, cooled to condense at least a portion of the light hydrocarbons and residual unreacted methanol, and passed to separator unit 46. This step recovers a $C_3$-$C_4$ LPG stream 47 containing less than 50 ppm methanol, suitable for further off-site fractionation in a gas plant. $C_2$- light off-gas 48 may be employed as fuel gas. The methanol-containing wash water extract stream 49 is then passed to FCC unit 50 for use in prewashing the $C_3$-$C_5$ etherification feedstock.

The following Example provides a detailed illustration of the process of this invention for a refinery operation processing methanol and $C_4$ feedstock to produce MTBE and hydrocarbon conversion products containing about 22 mole percent of gasoline products. At 900° F. reactor 40 temperature, the gasoline product is about 55 weight percent aromatics, 15 weight percent olefins, with the balance paraffins.

EXAMPLE

About 530.36 moles/hr of feedstock is passed to the etherification reactor system as described in FIG. 1. The feedstock contains 69 moles/hr of methanol and hydrocarbons consisting of 12 moles/hr of $C_3$'s, 129.45 moles/hr of isobutane, 219.18 moles/hr of 1-butene, 25.09 moles/hr of n-butane and 71.18 moles/hr of isobutene and 4.46 moles/hr of $C_5$+ hydrocarbons. Following etherification, the effluent therefrom contains 66.87 moles/hr of MTBE, 2.09 moles/hr of unreacted methanol, 4.27 moles/hr of unreacted isobutene, 12 moles/hr of $C_3$'s, 129.45 moles/hr of isobutane, 219.18 moles/hr of 1-butene, 25.09 moles/hr of n-butane and 4.46 moles/hr of $C_5$+. MTBE is recovered following debutanization and debutanized overhead vapor is passed to the fluidized bed zeolite conversion zone for contact with ZSM-5 catalyst under conversion conditions previously described in reference to FIG. 1. The conversion is carried out at a temperature of 480° C. (900° F.) and 925kPa (135 psia) to produce 354.16 moles/hr of effluent. The product stream consists essentially of water (2.09 moles/hr), $C_5$+ gasoline (77.87 moles/hr), isobutene (6.63 moles/hr), n-butane (39.21 moles/hr), 1-butene (6.63 moles/hr), isobutane (153.71 moles/hr), propane (37.98 moles/hr), propene (14.32 moles/hr), ethane (3.84 moles/hr), ethene (8.68 moles/hr), and methane (3.20 moles/hr).

PRIMARY STAGE—ETHERIFICATION OPERATION

The reaction of methanol with isobutylene and isoamylenes at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149-152, discusses the technology. A preferred catalyst is a polymeric sulfonic acid exchange resin such as Amberlyst 15.

In the etherification process it is known that alkanol and iso-olefins may be reacted in equimolar quantities or either reactant may be in molar excess to influence the complete conversion of the other reactant. Because etherification is an incomplete reaction the etherification effluent comprises unreacted alkanol and unreacted hydrocarbons. On a stoichiometric equivalencies basis, equimolar quantities of methanol and iso-olefins are advantageous but an excess between 2 and 100% of either component can be passed to the etherification reaction unit. In the present invention, the molar ratio of alkanol to iso-olefin, such as methanol to iso-butylene, can be between 0.7 and 2, but preferably the molar ratio is 1 for methanol to isobutylene. Advantageously, the excess methanol may be about 40% or more when the hydrocarbon feedstream comprises significant quantity of isoamylenes, but equimolar quantities are preferred when the hydrocarbon feedstream consists essentially of $C_4$ hydrocarbons.

Iso-olefins or isoalkenes in this invention are those having the formula $R_2C=CH_2$ or $R_2C=CHR$. Alkanols which may be used in the present invention include methanol, ethanol, 1-propanol, isopropanol, 1-butanol and 2-butanol. In this invention oxygenate or lower oxygenates refers to $C_1$-$C_5$ alcohols, ethers, aldehydes, esters and the like.

SECOND STAGE—METHANOL AND HYDROCARBONS CONVERSION

The methanol-containing etherification effluent stream, preferably a vapor stream, may be coreacted with olefinic light gas and/or other reactive hydrocarbon feedstreams in an oligomerization/aromatization reaction section, as described by Avidan et al. in U.S. Pat. Nos. 4,547,616 and 4,746,762 and by Owen et al. in U.S. Pat. Nos. 4,827,046 and 4,831,203, incorporated herein by reference. Optionally, light gas, containing ethene or propene may be injected at the bottom of the fluidized bed reaction zone and converted along with the unreacted methanol containing fractions of the light hydrocarbon etherification effluent stream.

It is advantageous to convert substantially the entire stream of unreacted alcohol and light olefinic components recovered from etherification effluent by acid zeolite catalysis, thus providing a once-through process without expensive alcohol recycle to the etherification unit. Zeolite conversion technology for upgrading lower aliphatic hydrocarbons and oxygenates to liquid hydrocarbon products, including gasoline boiling range hydrocarbons and aromatics, are well known. Commercial Methanol-to-Gasoline (MTG), methanol-to olefins (MTO), Mobil Olefin to Gasoline/Distillate (MOG/D) and conversion of olefins and paraffins to aromatics (M-2 Forming) processes employ shape selective medium pore zeolite catalysts. It is understood that the present zeolite conversion unit operation can have the characteristics of these catalysts and processes to produce a variety of hydrocarbon products, especially liquid aliphatics and aromatics in the $C_5$–$C_9$ gasoline range. The zeolite catalyzed conversion processes can be run in fixed, fluidized or moving catalyst beds.

The various reactions which take place in the zeolite conversion reactor include oligomerization, alkylation, dehydrocyclization, isomerization and cracking. These include exothermic and endothermic reactions, which can be thermally balanced to require little or no heat exchange to maintain process reaction temperature in the fluidized bed. Mixed hydrocarbons from FCC operations, following the etherification and effluent separation, can be selected or modified to include a balance of olefins and paraffins to achieve the desired thermodynamic properties.

DESCRIPTION OF ZEOLITE CATALYSTS

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, Fe or mixtures thereof, within the zeolitic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

Zeolite hydrocarbon upgrading catalysts preferred for use herein include the medium pore (i.e., about 5–7A) shape-selective crystalline aluminosilicate zeolites having a silica-to-alumina ratio of at least 12, a constraint index of about 1 to 12 and acid cracking activity (alpha value) of about 1 to 250, preferably about 3 to 80 based on total catalyst weight. In the fluidized bed reactor the coked catalyst preferably has an apparent activity (alpha value) of about 1 to 20 under the process conditions to achieve the required degree of reaction severity. Representative of the medium pore shape selective zeolites are ZSM-5, ZSM-11, ZSM-12, ZSM-23, ZSM-35, and ZSM-48. Aluminosilicate ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245; 4,414,423; 4,417,086; 4,517,396 and 4,542,251. The disclosures of these patents are incorporated herein by reference. While suitable zeolites having a coordinated metal oxide to silica molar ratio of 12:1 to 200:1 or higher may be used, it is advantageous to employ ZSM-5 having a silica alumina molar ratio of about 25:1 to 70:1, suitably modified if desired to adjust acidity and oligomerization/aromatization characteristics. A typical zeolite catalyst component having Bronsted acid sites may consist essentially of aluminosilicate ZSM-5 zeolite.

Certain of the ZSM-5 type medium pore shape selective catalysts are sometimes known as pentasils. In addition to the preferred aluminosilicates, the gallosilicate or the ferrosilicate materials may be employed. ZSM-5 type pentasil zeolites are particularly useful in the process because of their regenerability, long life and stability under the extreme conditions of operation. Usually the zeolite crystals have a crystal size from about 0.01 to 2 microns or more. In order to obtain the desired particle size for fluidization in the turbulent regime, the zeolite catalyst crystals are bound with a suitable inorganic oxide, such as silica, alumina, etc. to provide a zeolite concentration of about 5 to 95 wt.%. It is advantageous to employ a standard ZSM-5 having a silica:alumina molar ratio of 25:1 or greater in a once-through fluidized bed unit to convert 60 to 100 percent, preferably at least 75 wt %, of the monoalkenes and methanol in a single pass. In the preferred embodiment 25% H-ZSM-5 catalyst calcined with 75% silica-alumina matrix binder is employed unless otherwise stated.

FLUIDIZED BED REACTOR OPERATION

Suitable olefinic feedstreams to the olefin upgrading unit comprise $C_2$–$C_4$ alkenes, including unreacted butylenes and other alkenes from the etherification operation. Non-deleterious components, such as $C_4$ lower paraffins and inert gases, may be present. The reaction severity conditions can be controlled to optimize yield of olefinic gasoline or $C_6$–$C_8$ BTX hydrocarbons, according to product demand. Reaction temperatures and contact time are also significant factors in the reaction severity, and the process parameters are followed to give a substantially steady state condition wherein the reaction severity is maintained within the limits which yield a desired weight ratio of propane to propene in the reaction effluent.

In a turbulent fluidized catalyst bed the conversion reactions are conducted in a vertical reactor column by passing hot reactant vapor or lift gas upwardly through the reaction zone at a velocity greater than dense bed transition velocity and less than transport velocity for the average catalyst particle. A continuous process is operated by withdrawing a portion of coked catalyst from the reaction zone, oxidatively regenerating the withdrawn catalyst and returning regenerated catalyst to the reaction zone at a rate to control catalyst activity and reaction severity to effect feedstock conversion. However, the processes may be operated without employing a catalyst regenerator.

In a typical process, the alkanol and olefinic feedstream is converted in a catalytic reactor under oligomerization conditions and moderate pressure (i.e., 100 to 2500 kPa) to produce a predominantly liquid product consisting essentially of $C_5+$ hydrocarbons rich in gasoline-range mono-olefins and aromatics. The $C_5+$ gasoline product comprises at least 20 weight percent aromatics at temperatures higher than 750° F. and WHSV lower than 3. The use of fluidized bed catalysis allows excellent control of catalyst activity and temperature which can be used to maintain relatively constant product quality. In addition, it provides excellent flexibility to change operating conditions.

The light aliphatic hydrocarbon conversion process to form aromatics may utilize conversion conditions described in U.S. Pat. No. 3,760,024 (Cattanach); U.S. Pat. No. 3,845,150 (Yan and Zahner); U.S. Pat. No. 4,097,367 (Haag et al.); U.S. Pat. No. 4,350,835 (Chester et al.); U.S. Pat. No. 4,590,323 (Chu); and U.S. Pat. No. 4,629,818 (Burress) incorporated herein by reference. Preferred aromatization conditions include temperatures of about 400° C.–600° C. and pressure from about 100–2000 kPa, absence of hydrogen and a weight hourly space velocity of from 0.5 to 20 WHSV. The $C_6$–$C_{10}$ aromatic products which are produced are predominantly benzene, toluene and xylene isomers (BTX) with minor amounts of other $C_6$–$C_{10}$ components.

Effluent from the olefin upgrading reactor (40) includes minor amounts of oxygenates derived from excess methanol employed in etherification. These impurities may include $C_1$–$C_5$ volatile components, including alkanol, ketone, aldehyde and carboxylic acid. A typical second stage reactor effluent from zeolite conversion of MTBE primary stage effluent $C_4$- overhead is given in Table 1. The acidic nature of the reactor's effluent may require that the exposed downstream distillation equipment be constructed of 316 stainless steel or the like. Typical design criteria should allow for at least 18 ppm acid concentration in the overhead raffinate and/or bottom streams. It is understood that the acid may be neutralized by injection of ammonia or other base.

TABLE 1

| Oxygenates Concentration In MOG Reactor Effluent, ppm | | |
|---|---|---|
|  | Typical | Range |
| Acetone | 30 | 0–90 |
| Methanol | 3 | 1–20 |
| Ethanol | 1 | 1–20 |
| 2-Propanol | 1 | 0.1–20 |
| Acetaldehyde | 2 | 1–10 |
| N-Propanal | 0.1 | 0–1 |
| Methyl Ethyl Ketone | 4 | 1–20 |
| 2-Pentanone | 1 | 0–10 |
| Formic Acid | 0.4 | 0.2–1 |
| Acetic Acid | 1 | 0.1–4 |
| Propionic Acid | 0.4 | 0.2–1 |
| Butyric Acid | 0.1 | 0.0–0.2 |

ALTERNATIVE EMBODIMENT

Figure 2:
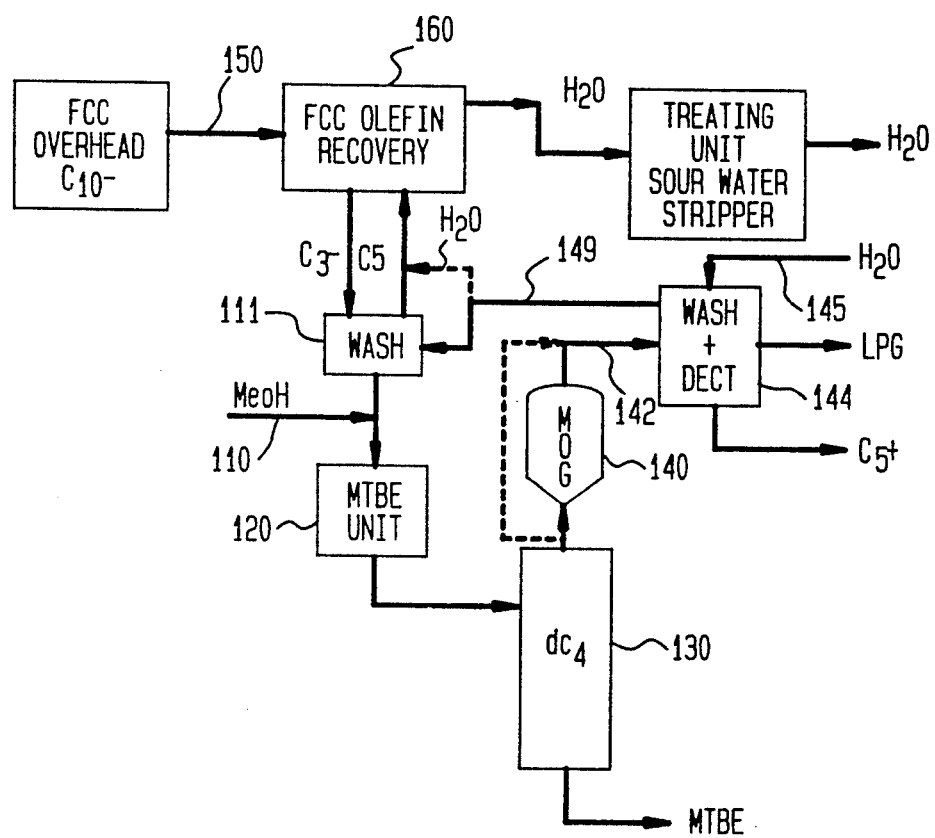
FIG. 2 is a process flow diagram of alternative embodiments.

The embodiment in FIG. 2 is similar to FIG. 1, simplified to omit details and employing the same ordinal numbering. Process stream options are shown in dashed line. Methanol 110 is fed along with washed hydrocarbon from unit 111 to etherification unit 120. MTBE reaction effluent is distilled in debutanizer unit 130 to recover ether product and an olefin-methanol overhead for reaction in upgrading "MOG" reactor 140 to obtain olefinic effluent stream 142. This stream is treated in debutanizer wash unit 144 where an aqueous stream 145 is introduced. Washed LPG and $C_5+$ streams are recovered and oxygenate-containing water stream 149 is fed to a pretreatment wash unit 111 for contact with olefinic FCC hydrocarbons in the $C_3$–$C_5$ range and rich in tertiary olefins. Thus the wash water may be employed advantageously for pretreating MTBE feedstock to remove impurities present in the main FCC overhead stream 150. FCC light olefins are recovered in conventional separation unit 160. Optionally, stream 149 is passed to the FCC olefin recovery unit 160. Wash water stream 149 may be passed through unit 160 prior to disposal or treatment in a sour water stripper unit.

Any alkanol containing water extract stream described in this invention can be sent to a refinery hydrocarbon recovery section such as FCC gas plant to recover alkanol from water. This extract stream can behave as wash water used in the refinery hydrocarbon recovery section.

While the instant invention has been described by specific examples and embodiments, there is no intent to limit the inventive concept except as set forth in the following claims.

We claim:

1. A process for reacting methanol feedstock with light washed olefinic hydrocarbons rich in isobutylene to produce $C_5+$ alkyl tertiary-alkyl ether, which comprises:

a) contacting dry methanol feedstock with olefinic hydrocarbon feedstock comprising predominantly isobutylene-rich mono-olefins in a primary stage having a catalytic reaction zone maintained under etherification reaction conditions in the presence of acid etherification catalyst to produce a primary stage effluent comprising ether product, unreacted methanol and light olefins;

b) separating ether product from primary stage effluent unreacted methanol and light olefins to provide a light etherification effluent stream containing the unreacted methanol and light olefins;

c) converting at least a major portion of said unreacted methanol and light olefins to $C_5+$ gasoline boiling range hydrocarbons in a secondary stage reaction zone in contact with acidic medium pore metallosilicate catalyst;

d) separating secondary stage conversion effluent to recover a secondary light hydrocarbon stream comprising water-soluble oxygenates and light hydrocarbons and a liquid $C_5+$ hydrocarbon product stream;

e) contacting the secondary light hydrocarbon stream with a substantially fresh water liquid extract stream to remove water-soluble oxygenates; and f) passing at least a portion of oxygenate-containing liquid extract stream from step e) for washing pretreatment of hydrocarbon feedstock to the primary stage.

2. The process of claim 1 wherein said light olefinic hydrocarbon stream consists essentially of $C_4$ olefins and paraffins rich in isobutylene.

3. The process of claim 1 wherein secondary stage reaction conditions comprise temperature between 400° and 600° C., pressure between 100 and 2000 kPa; and wherein said metallosilicate catalyst comprises acidic, medium pore zeolite.

4. The process of claim 1 wherein secondary stage effluent is separated in a debutanizer distillation unit and fresh wash water is added to debutanizer overhead vapor to extract oxygenates in a condensed liquid extract stream.

5. A continuous process for converting dry lower aliphatic alkanol and light olefinic hydrocarbon feedstock rich in isobutylene and/or isoamylene to alkyl tertiary-alkyl ethers comprising the steps of:
 a) washing the olefinic hydrocarbon feedstock with an aqueous liquid stream in a contactor unit to recover water-soluble impurities therefrom in a washwater stream recovered from the contactor unit;
 b) thereafter contacting the dry lower aliphatic alkanol and a washed light olefinic hydrocarbon stream from the contactor unit under iso-olefin etherification conditions in at least one etherification reaction zone containing acid etherification catalyst;
 c) distilling etherification effluent to recover a light primary effluent stream comprising unreacted alkanol and light olefinic hydrocarbon and a liquid product stream containing alkyl tertiary-alkyl ether;
 d) contacting unreacted alkanol and light olefinic hydrocarbon stream with a substantially fresh water liquid extractant stream to recover unreacted alkanol therein and passing a portion of the liquid extractant stream to step c) as reflux;
 e) passing a portion of the alkanol-containing liquid extract stream to the washing step a) for treatment of hydrocarbon feedstock; and
 f) passing at least a portion of the alkanol-containing liquid extract stream from step d) and/or e) to a refinery light olefin recovery process for washing and removing water-soluble impurities from refinery light olefin.

6. The process of claim 5 wherein said alkanol includes methanol, ethanol, 1-propanol, isopropanol, 1-butanol, 2-butanol or mixtures thereof.

7. The process of claim 5 wherein the alkanol feedstock comprises dry methanol and wherein the hydrocarbon consists essentially of $C_3-C_5$ paraffins and olefins.

8. The process of claim 5 wherein the alkyl tertiary-alkyl ether comprises methyl tertiary butyl ether and/or methyl tertiary amyl ether.

9. The process of claim 5 wherein said light hydrocarbon stream comprises about 80 weight percent mixed butanes and butenes.

10. The process of claim 5 wherein said alkanol comprises methanol.

11. A process for reacting methanol feedstock with light olefinic hydrocarbons containing at least one tertiary olefin to produce $C_5+$ alkyl tertiary-alkyl ether and $C_5+$ hydrocarbons, which comprises:
 a) washing the olefinic hydrocarbon feedstock with an aqueous liquid stream to recover water-soluble impurities therefrom in a washwater stream;
 b) contacting the methanol and washed olefinic hydrocarbon stream under iso-olefin etherification conditions in an etherification reaction zone containing acid etherification catalyst;
 c) separating ether product from unreacted methanol and light olefinic hydrocarbons;
 d) converting at least a major portion of said unreacted methanol and olefinic hydrocarbons to $C_5+$ gasoline boiling range hydrocarbons in contact with acidic medium pore metallosilicate catalyst;
 e) separating step (d) conversion effluent to recover a liquid $C_5+$ hydrocarbon product stream and a light effluent stream comprising unreacted methanol and other oxygenates with light hydrocarbon;
 f) contacting said light effluent stream with a substantially fresh water liquid extractant stream to recover unreacted methanol and oxygenates therein.

12. The process of claim 11 including the additional step of (g) passing at least a portion of the methanol-containing liquid extract stream to the washing step for treatment of hydrocarbon feedstock.

13. The process of claim 11 wherein said light olefinic hydrocarbon stream consists essentially of $C_4$ olefins and paraffins; and wherein said unreacted methanol and olefinic hydrocarbons conversion conditions in step (d) comprise temperature between 400° and 600° C., and pressure between 100 and 2000 kPa.

14. The process of claim 13 wherein said metallosilicate catalyst comprises acidic, medium pore zeolite.

15. The process of claim 11 including the step of passing at least a portion of the liquid extract stream containing oxygenates to a hydrocarbon cracking unit.

16. The process of claim 15 wherein the liquid extract stream is passed to a refinery hydrocarbons recovery section.

17. The process of claim 16 wherein the liquid extract stream is passed to an FCC (Fluid Catalytic Cracking) gas separation plant.

18. The process of claim 13 wherein step (e) light effluent stream includes oxygenate comprising water-soluble ketone, aldehyde or alkanoic acid.

19. The process of claim 1 including the step of recovering from step e) a liquid extract stream, and passing at least a portion of said liquid extract stream to a refinery hydrocarbons recovery section for washing light olefinic hydrocarbons.

20. The process of claim 10 wherein the liquid extract stream is passed to a gas separation plant.

21. A process for reacting dry alkanol with light olefinic hydrocarbon rich in tertiary olefin to produce $C_5+$ alkyl tertiary-alkyl ether, which comprises:
 contacting dry alkanol feedstock with light olefinic hydrocarbon feedstock comprising tertiary olefin in a primary stage having a catalytic reaction zone maintained under etherification reaction conditions in the presence of acid etherification catalyst to produce etherification effluent comprising ether product, water-soluble oxygenates including unreacted alkanol, and light olefin;
 distilling etherification effluent unreacted alkanol and light olefins to provide an overhead distillation stream containing said water-soluble oxygenates and light olefins and a bottom distillation stream;
 contacting water-soluble oxygenates including unreacted alkanol, and light olefin in the overhead distillation stream with water to remove water-soluble oxygenates in an aqueous extract stream; and
 passing at least a portion of the aqueous extract stream to a petroleum refinery gas separation unit for washing treatment of olefinic hydrocarbon.

22. The process of claim 21 including the steps of separating etherification effluent in a distillation unit wherein fresh wash water is added to the overhead distillation stream to extract oxygenates in a condensed liquid extract stream; and passing a portion of said condensed liquid extract stream as reflux to the distillation unit.

23. The process of claim 21 wherein said alkanol comprises methanol, ethanol, 1-propanol, isopropanol, 1-butanol, 2-butanol or mixtures thereof; and wherein said tertiary olefin comprises isobutylene and/or isoamylene.

24. The process of claim 21 wherein the alkanol comprises methanol and wherein the hydrocarbon consists essentially of $C_3$–$C_5$ paraffins and olefins; wherein the alkyl tertiary-alkyl ether comprises methyl tertiary butyl ether and/or methyl tertiary amyl ether.

25. The process of claim 21 wherein etherification stage effluent is separated in a debutanizer distillation unit and water is added to debutanizer overhead vapor to extract oxygenates in a condensed aqueous liquid extract stream.

* * * * *